United States Patent
Garai et al.

(10) Patent No.: US 11,806,503 B2
(45) Date of Patent: Nov. 7, 2023

(54) REMOVABLE WEARABLE DEVICE AND RELATED ATTACHMENT METHODS

(71) Applicant: MEDTRONIC MINIMED, INC., Northridge, CA (US)

(72) Inventors: Ellis Garai, Studio City, CA (US); Ravi R. Deverkadra, Simi Valley, CA (US); Jacob E. Pananen, Santa Monica, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 375 days.

(21) Appl. No.: 17/084,529

(22) Filed: Oct. 29, 2020

(65) Prior Publication Data

US 2022/0133988 A1    May 5, 2022

(51) Int. Cl.
*A61M 5/142*       (2006.01)
*A61F 13/02*       (2006.01)
*A61F 13/00*       (2006.01)

(52) U.S. Cl.
CPC ..... *A61M 5/14248* (2013.01); *A61F 13/0246* (2013.01); *A61F 2013/00417* (2013.01)

(58) Field of Classification Search
CPC .............. A61M 5/14248; A61B 5/6833; A61F 13/0246; A61F 2013/00417
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,772,623 A * | 6/1998 | Conte ................. A61F 13/0246 602/57 |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |

(Continued)

FOREIGN PATENT DOCUMENTS

| | | |
|---|---|---|
| WO | 2019210240 A1 | 10/2019 |
| WO | 2019222615 A1 | 11/2019 |

OTHER PUBLICATIONS

Qilan Li, A Practical Fabrication Method of the Gecko-Inspired Easy-Removal Skin Adhesives, University of Twente, Department of Engineering Technology, Laboratory for Surface Technology and Tribology, Dec. 7, 2016, https://www.sciencedirect.com/science/article/pii/S2405451816300502.

(Continued)

*Primary Examiner* — Laura A Bouchelle
(74) *Attorney, Agent, or Firm* — Foley & Lardner LLP (57) ABSTRACT

Removable devices wearable on a user's skin and methods for using such devices are provided. An exemplary removable device includes a skin adhesive configured to adhere to the skin, a durable component, and an interface component interconnecting the durable component and the skin adhesive. The device separates at the interface component to remove the durable component from the skin adhesive upon application of a removal force to the device.

26 Claims, 8 Drawing Sheets

(56) References Cited

U.S. PATENT DOCUMENTS

| | | |
|---|---|---|
| 6,175,752 B1 | 1/2001 | Say et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,021 B2* | 2/2012 | Robertson ............ A61M 5/172 600/300 |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,592,640 B2 | 11/2013 | Zepeda et al. |
| 10,010,675 B2* | 7/2018 | Cabiri ................ A61M 5/3202 |
| 10,285,617 B2 | 5/2019 | Toth et al. |
| 10,335,302 B2 | 7/2019 | Perez et al. |
| 2004/0116866 A1* | 6/2004 | Gorman ............ A61M 5/14248 604/93.01 |
| 2006/0211970 A1* | 9/2006 | Sciulli ................ A61F 13/0269 602/41 |
| 2007/0123819 A1 | 5/2007 | Mernoe et al. |
| 2008/0214914 A1 | 9/2008 | Say et al. |
| 2010/0160861 A1 | 6/2010 | Causey, III et al. |
| 2014/0378799 A1* | 12/2014 | Chattaraj ................ B32B 7/12 600/300 |
| 2016/0058380 A1* | 3/2016 | Lee ..................... A61B 5/6832 600/365 |
| 2016/0361015 A1 | 12/2016 | Wang et al. |
| 2017/0258402 A1 | 9/2017 | Acquista et al. |
| 2020/0109314 A1 | 4/2020 | Merrill et al. |
| 2020/0155050 A1 | 5/2020 | Pryor et al. |

OTHER PUBLICATIONS

Vitalconnect, VistaPoint 2.1 QuickStart and Instructions for Use, VitalConnect, Inc., Nov. 2019, https://vitalconnect.com/docs/ifu015/revB/IFU-15,%20VistaPoint%202.1,%20Rev.%20B.pdf.

Bryan Laulicht, et. al., Quick-Release Medical Tape, PNAS, vol. 109, No. 46, Nov. 30, 2012, pp. 18803-18808, https://www.ncbi.nlm.nih.gov/pmc/articles/PMC3503228/pdf/pnas.201216071.pdf.

* cited by examiner

REMOVABLE WEARABLE DEVICE AND RELATED ATTACHMENT METHODS

TECHNICAL FIELD

The present technology is generally related to wearable devices and components, such as medical devices, and more particularly, to the removal of wearable devices that are adhered to the skin.

BACKGROUND

Certain chronic diseases can be monitored and treated in a continuous manner or at particular times throughout the day using medical devices that externally attach to the body. Medical devices that are connected to the body externally require a robust and stable connection that can last for one or more days of wear while providing consistent and accurate monitoring or treatment.

For example, a patient can utilize external sensor devices that connect a sensor to the body to monitor his or her condition. The connection of external sensor devices to the body must be stable to obtain accurate physiological readings of the patient. Delivery devices can also be externally connected to the body to deliver medication. The connection of external delivery devices to the body must be steady enough to allow consistent fluid-flow communication of the medication from the device to the body. If the attachment of the delivery device to the body is disrupted, loss of medication can occur or inaccurate dosages of medication can be delivered to the body.

As a non-limiting example, diabetic patients monitor their blood glucose (BG) levels and deliver insulin continuously or at certain times throughout the day utilizing external devices. The diabetic patient measures his or her BG level using a BG measurement device to determine if treatment is needed, be it with glucose to raise glucose levels or insulin to lower glucose levels. The diabetic patient may use a continuous glucose measurement or monitoring system to monitor sensor glucose (SG) throughout the day. To deliver the insulin to the body, the diabetic patients use insulin delivery devices, including external infusion pumps or patches. Both monitoring and delivery devices should be connected to the body in a stable manner to obtain accurate sensor readings and provide correct delivery dosages.

Current methods of attaching medical devices to the skin or body of the patient utilize adhesive. The adhesive is applied on the device and adheres to the body. Adhesive methods of attachment alone can lose effectiveness in adhering to the body for patients living in geographical areas of high humidity or for patients living active lifestyles. Because of the instability of the attachment of the external device to the body, the operation of devices, which are sensitive to movement, can be compromised. The devices can detach and fall off the body due to lack of adhesion and the patients are thus not able to utilize the important diagnostic and therapeutic tools. Again, the devices can provide inaccurate sensor readings and send erroneous data to a delivery device, or could result in loss of medication at the delivery site into the body. The current methods of attachment of external devices also do not address the problems associated with anchoring a rigid inflexible device to the body for the desired length of time and easily removing the device thereafter.

Accordingly, it is desirable to provide removable wearable devices and methods that improve performance and provide ease of use.

BRIEF SUMMARY

The subject matter of this discloses generally relates to removable devices wearable on a user's skin and methods for using such devices. In one aspect, the present disclosure provides an exemplary removable device including a skin adhesive configured to adhere to the skin, a durable component, and an interface component interconnecting the durable component and the skin adhesive. The device separates at the interface component to remove the durable component from the skin adhesive upon application of a removal force to the device.

In another aspect, the present disclosure provides a removable device wearable on a user's skin includes a skin adhesive configured to adhere to the skin, the skin adhesive having a periphery, a first region with a first adhesive strength, and a second region with a second adhesive strength less than the first adhesive strength that is directly adjacent to the periphery. The removable device further includes a durable component and an interface component interconnecting the durable component and the skin adhesive. The device separates at the interface component to remove the durable component from the skin adhesive upon application of a removal force to the device.

In another aspect, the present disclosure provides a method for using a removable medical device. The method includes adhering the device to a user's skin. The device includes a skin adhesive in direct contact with the user's skin, a durable component, and an interface component interconnecting the durable component and the skin adhesive. The method further includes separating the device at the interface component and removing the durable component from the skin adhesive. Also, the method includes treating the skin adhesive and removing the skin adhesive from the user's skin.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In addition, certain terminology may also be used in the following description for the purpose of reference only, and thus are not intended to be limiting. For example, terms such as "underlying", "upper", "lower", "above", and "below" refer to directions in the drawings to which reference is made. Terms such as "top", "bottom", "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

Embodiments herein are drawn to a removable device including a plurality of nonwoven and fastener material layers. In certain embodiments, adhesive bonding, backing adhesive, transfer adhesive, pressure sensitive adhesive, polyurethane medical tape, humidity-resistant adhesive, UV cure adhesive, ultrasonic welding, and/or other like attachment methods can be used to attach the plurality of layers of the device to one another. Apparent from the accompanying figures, the drawings of the device are not drawn to scale.

For use with certain types of wearable devices, the skin adhesive must be necessarily strong to provide for adhesion times of two weeks or more. As a result, it can be difficult and painful to remove a device secured with such skin adhesive from the skin. As described herein, a removable device is provided with an engineered "weakness" between the skin adhesive and other portions of the device. Specifically, an interface component is located between a rigid component (such as a durable component) and the skin adhesive that provides for the use of less force to first remove the durable component while the skin adhesive remains on the skin. In particular, the durable component is secured to the skin adhesive with less adhesive force than the skin adhesive is secured to the skin with. With the durable component removed, greater access to the skin adhesive is provided. Thus, it may be easier to peel the skin adhesive from the skin. Further, the skin adhesive may be treated to reduce the adhesive force, such as by UV light or solvents.

Embodiments described herein may be utilized in conjunction with medical devices, such as wearable, portable electronic medical devices. The medical device can be configured to provide monitoring or treatment operation on a user while attached to the body. Medical devices that can utilize various embodiments described herein include, but are not limited to, sensors, physiological characteristic monitors and infusion medium delivery systems, devices and methods that can include cannula or needle inserting devices and methods. Although many different applications are possible, exemplary embodiments are used in applications that incorporate a continuous glucose monitoring (CGM) system. That said, the subject matter described herein is not limited to use with such system (or any particular configuration or realization thereof).

Devices according to embodiments herein can be used with, connectable to and disconnectable from or incorporated in a portion of a medical device system. As a non-limiting example, a needle inserting device can be connected to a base structure of an infusion delivery device for insertion of a needle, after which the needle inserting device can be removed from the base and replaced with a different device component such as, but not limited to a reservoir and pump or drive device can be coupled to the base for operation. For example, a sensor or delivery medical device and method may operate to insert a cannula or needle through a user's skin to convey a fluid from the user to one or more sensor elements and/or to provide a fluid flow path for conveying an infusion medium through a hollow channel in the cannula or needle and into the user. Embodiments can also be configured to provide a contiguous fluid-flow passage for fluid transfer between a reservoir and the user when the hollow needle or cannula is inserted in the user. For example, the user could use the device and method with infusion delivery systems. As a non-limiting example, the device can be used with any insulin infusion pump, patch, insulin infusion set and the like that is used externally on the body of a user. The device could also be used with patch devices generally described by way of example in U.S. Pat. No. 8,323,250 filed Feb. 7, 2008, entitled "Adhesive patch systems and methods," the disclosure of which is herein incorporated by reference in its entirety.

In some embodiments, the medical device can include one or more components. In embodiments, at least a portion of a medical device can be adapted to be secured to the user during operation of the medical monitoring or treatment device and another portion of the medical device may be removable during operation of the device. Certain embodiments may be directed to use of the device and method with a sensor monitoring system. Such embodiments can be used with a sensor having a sensor base with a cannula that can be inserted into the skin of a user and a sensor transmitter that is connectable to and disconnectable from the sensor base while the base remains attached to the skin. The sensor can provide a signal indicative of a characteristic of a user and may be implanted in and/or through subcutaneous, dermal, sub-dermal, inter-peritoneal or peritoneal tissue. Embodiments of a surface mounted sensor could utilize interstitial fluid harvested from underneath the skin. In specific embodiments, the sensor can determine glucose levels in the blood and/or body fluids of the user. However, it will be recognized that further embodiments may be used to determine the levels of other agents, characteristics or compositions, such as hormones, cholesterol, medication concentrations, pH, oxygen saturation, viral loads (e.g., HIV), or the like. Embodiments may provide sensor readings on an intermittent or continuous basis.

The sensor can be an electrode-type sensor, or other type of sensor, such as chemical based, optical based or the like. The sensor transmitter can store and provide sensor readings to other devices or other components of a sensor system. For example, the transmitter can process and wirelessly transmit sensor signals to a remotely located data receiving device. Some embodiments can allow a user or a physician to disconnect the sensor transmitter from the sensor base to retrieve sensor readings. In other embodiments, the sensor controller and/or sensor transmitter used with the device need not be disconnected from the sensor base during operation and can be connected for the entire duration of wear. In further embodiments, the sensor base and sensor transmitter can be manufactured as one medical device instead of multiple components.

Figure 1:
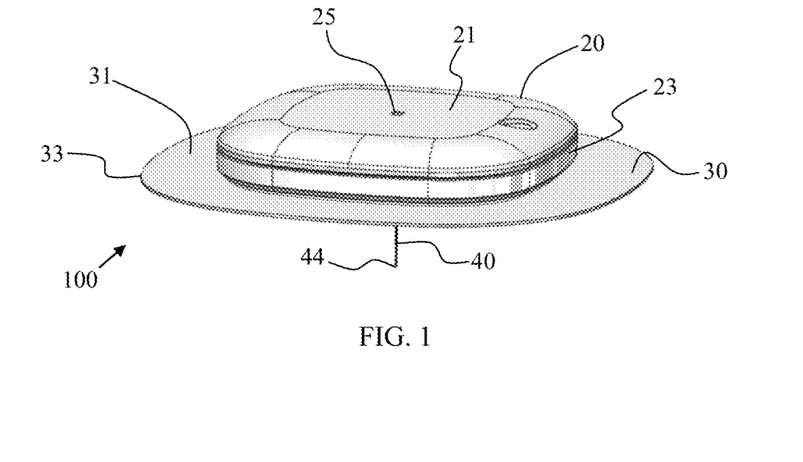
FIG. 1 is a perspective view of a removable monitoring device in accordance with embodiments herein.

Referring now to FIG. 1, a removable device 100, such as an analyte monitoring device, is illustrated. In an exemplary embodiment, the device 100 is part of a continuous glucose monitoring system. As shown, device 100 includes a durable component 20, such as a transmitter. As shown, the durable component 20 is formed with a housing having a top side 21 and an opposite bottom side (not shown in FIG. 1) and extends to and terminates at a periphery 23. A central opening 25 is formed in the durable component housing and extends from the top side 21 to the bottom side.

The exemplary device 100 further includes an adhesive 30 for adhering the device 100 to a user's skin, i.e., a skin adhesive 30. The skin adhesive 30 has a top side 31 and an opposite bottom side (not shown in FIG. 1) and extends to and terminates at a periphery 33. An exemplary skin adhesive 30 is pressure sensitive skin adhesive such as an acrylic adhesive, though other suitable adhesives may be used.

Also, the device 100 includes a sensor 40 extending downward from the durable component 20 to a distal end 44. The central opening 25 may receive a needle or probe to insert the sensor 40 into the user's skin, i.e., for subcutaneous implantation.

Figure 2:
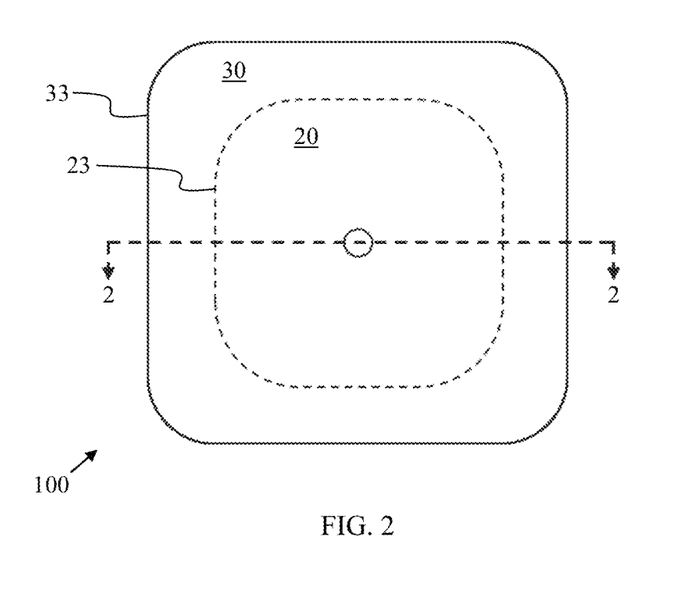
FIG. 2 is a plan overhead view of the removable monitoring device of FIG. 1.

FIG. 2 is an overhead plan view of the device 100 of FIG. 1. As shown, the entirety of the durable component 20 lies over the skin adhesive 30, i.e., a footprint defined by the periphery 23 of the durable component 20 is located within an area bounded by the periphery 33 of the skin adhesive 30.

Figure 3:
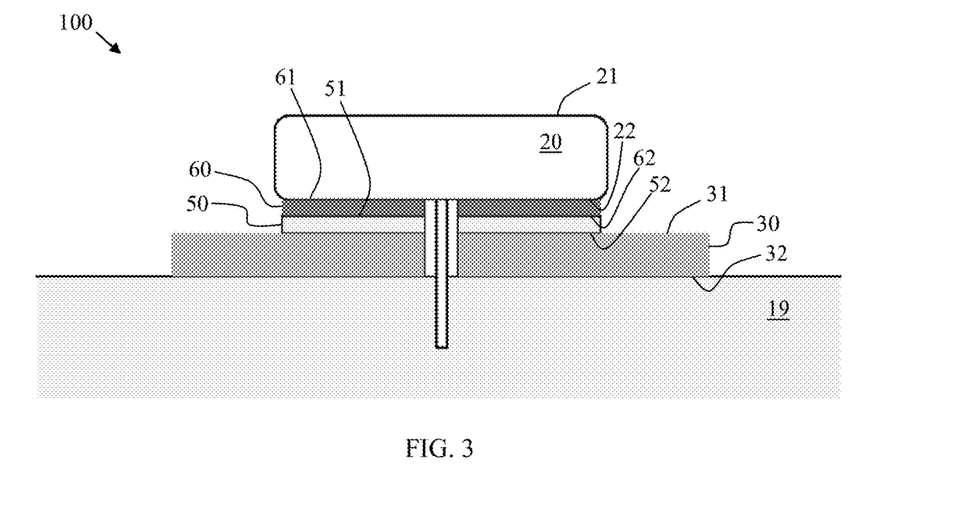
FIG. 3 is a cross-sectional view of the removable monitoring device of FIG. 2.

FIG. 3 provides a cross-section view of the device 100 of FIG. 2, generalized and taken along line 2-2 in FIG. 2. In FIG. 3, the device 100 is worn on the skin 19 of a user with the bottom side 32 of the skin adhesive 30 in direct contact with and adhering to the skin 19.

Above the top side 31 of the skin adhesive 30 and below the bottom side 22 of the durable component 20, the device 100 includes an adhesive 50 for adhering the durable component 20 to the skin adhesive 30, i.e., an intermediate adhesive 50. The intermediate adhesive 50 includes a top side 51 and an opposite bottom side 52. An exemplary intermediate adhesive 50 is a double-sided pressure sensitive adhesive.

Also, above the top side 31 of the skin adhesive 30 and below the bottom side 22 of the durable component 20, the device 100 includes an interface component 60. The interface component 60 includes a top side 61 and an opposite bottom side 62.

The device 100 is designed to separate along the interface component 60 to allow the durable component 20 to be removed from the skin adhesive 30 before the skin adhesive 30 is removed from the skin 19. FIG. 3 illustrates that the interface component 60 is located between the intermediate adhesive 50 and the durable component 20; however, the interface component 60 may instead be located between the intermediate adhesive 50 and the skin adhesive 30.

Figure 4:
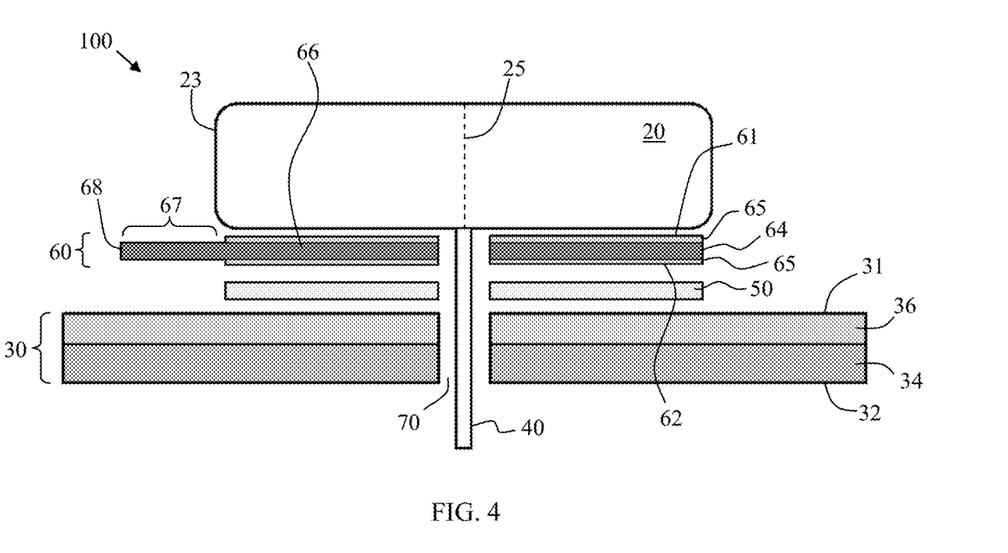
FIG. 4 is an exploded, detailed cross-sectional view of the removable monitoring device of FIG. 3.

FIG. 4 provides an exploded cross-sectional view of the device 100 of FIG. 3 including more specificity regarding exemplary embodiments. As shown, the exemplary skin adhesive 30 includes an adhesive layer 34 forming the bottom side 32 and a backing layer 36 forming the top side 31. As noted above, adhesive layer 34 may be formed from any suitable adhesive, such as a pressure sensitive skin adhesive like an acrylic adhesive. The backing layer 36 may be a nonwoven polyurethane or other suitable material.

Further, the exemplary interface component includes a substrate 64 and an interface adhesive 65. An exemplary substrate 64 is a substrate such as a synthetic tear resistant paper. An exemplary interface adhesive 65 is a double-sided pressure sensitive adhesive. In the illustrated embodiment, the interface adhesive 65 is located on the top and bottom of the substrate 64 such that the interface adhesive 65 forms both the top side 61 and the bottom side 62 of the interface component 60. Alternatively, the interface adhesive 65 may be located on only one side of the substrate 64 such that the substrate 64 forms one of the sides 61 or 62 of the interface component 60. In exemplary embodiments, each side of the substrate 64 is in contact with an adhesive—either with both sides in contact with the interface adhesive 65, as shown, or with one side in contact with the interface adhesive 65 and the other side in contact with the intermediate adhesive 50.

FIG. 4 illustrates that the interface component 60, and more specifically the substrate 64, includes a central or main portion 66 lying directly below the durable component 20, i.e., within the footprint bounded by the periphery 23 of the durable component, and an extension or tab portion 67 that lies laterally outward from the main portion 66 and not within the footprint of the durable component 20. In other words, the interface component 60, and more specifically the substrate 64, extends from within the footprint to outside the footprint, i.e., outward from below the durable component 20 to an end 68 that is outside the footprint of the durable component 20 to provide a tab for a user to grasp for application of a removal force to the device.

Further, in FIG. 4, each of the skin adhesive 30 (including the adhesive layer 34 and the backing layer 36), the intermediate adhesive 50, the interface component 60 (including the substrate 64 and the interface adhesive 65) is formed with a central void 70. The central voids 70 of these members are aligned with one another and are aligned with the central opening 25 in the durable component 20. As shown, the sensor 40 is located in the central voids 70 for insertion into a user's skin.

As may be understood from FIG. 4, when in use the bottom side 32 of the adhesive layer 34 of the skin adhesive 30 directly contacts and adheres to the skin 19, the adhesive layer 34 directly contacts the backing layer 36, the top side 31 of the backing layer 36 of the skin adhesive 30 directly contacts and is adhered to the intermediate adhesive 50, the intermediate adhesive 50 directly contacts and adheres to the bottom side 62 of the interface component 60 (and specifically to the interface adhesive 65), and the top side 61 of the interface component 60 (specifically the interface adhesive 65) directly contacts and adheres to the bottom side 22 of the durable component 20. Thus, in the embodiment of FIG. 4, the intermediate adhesive 50 directly interconnects the backing layer 36 of the skin adhesive 30 and the interface component 60.

Figure 5:
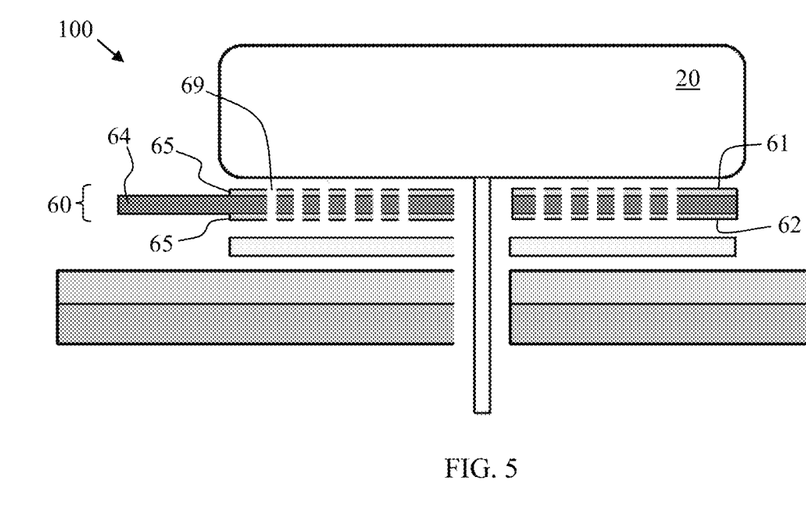
FIG. 5 is an exploded, detailed cross-sectional view of a removable monitoring device in accordance with embodiments herein.

FIG. 5 illustrates an exemplary embodiment of device 100. In FIG. 5, the interface component 60 is formed with channels 69 to improve breathability of the interface component 60. Such channels 69 may be formed as spaced apart perforations or in other suitable arrangements providing for sufficient structural integrity of the interface component 60, i.e., the interface component 60 will not tear during use due to the arrangement of the channels 69. As shown, each channel 69 extends from the top side 61 to the bottom side 62 of the interface component 60.

Figure 6:
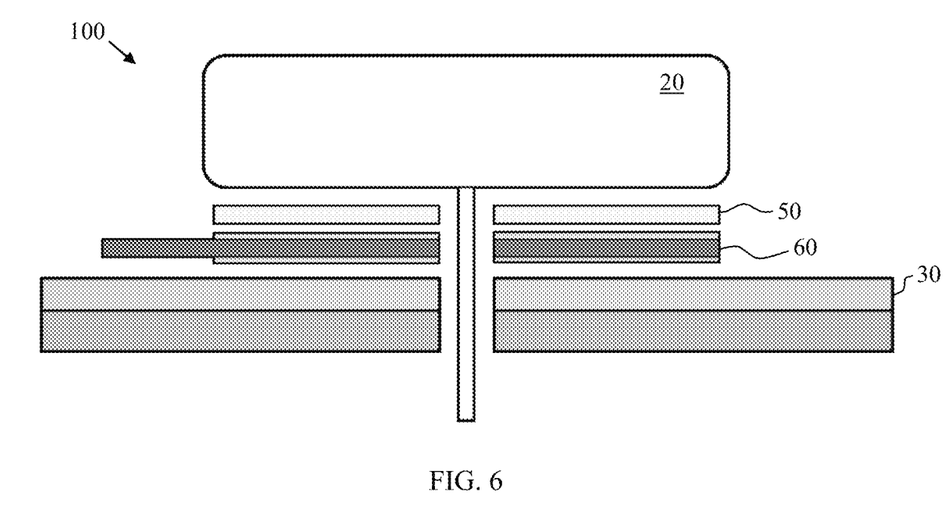
FIG. 6 is an exploded, detailed cross-sectional view of a removable monitoring device in accordance with embodiments herein.

FIG. 6 illustrates an embodiment in which, as referenced above, the interface component 60 is located between the skin adhesive 30 and the intermediate adhesive 50, rather than between the intermediate adhesive 50 and the durable component 20 as illustrated above. It is noted that the various features of the illustrated embodiments may be combined as desired and feasible. For example, a device 100 as illustrated in FIG. 6 may include an interface component 60 with the channels 69 illustrated in FIG. 5.

Cross-referencing FIG. 6 with FIG. 4, it may be understood that in the embodiment of FIG. 6, when in use the bottom side 32 of the adhesive layer 34 of the skin adhesive 30 directly contacts and adheres to the skin 19, the adhesive layer 34 directly contacts the backing layer 36, the top side 31 of the backing layer 36 of the skin adhesive 30 directly contacts and is adhered to the bottom side 62 of the interface component 60 (and specifically to the interface adhesive 65), the top side 61 of the interface component 60 (specifically the interface adhesive 65) directly contacts and adheres to the intermediate adhesive 50, and the intermediate adhesive 50 directly contacts and adheres to the bottom side 22 of the durable component 20. Thus, in the embodiment of FIG. 6, the intermediate adhesive 50 directly interconnects the interface component 60 and the durable component 20.

Figure 7:
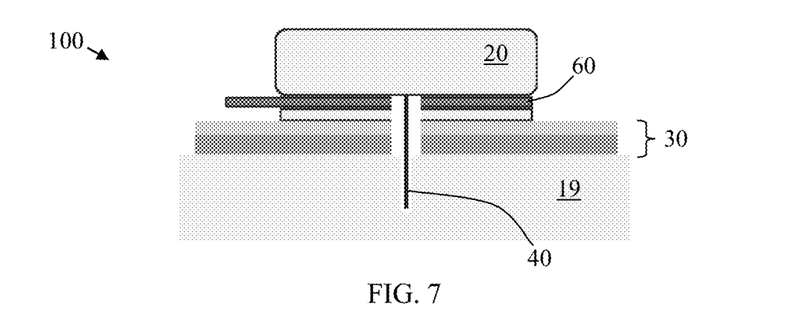
FIGS. 7-9 are cross-sectional views of a removable monitoring device in accordance with embodiments herein illustrating method steps for use thereof.
Figure 8:
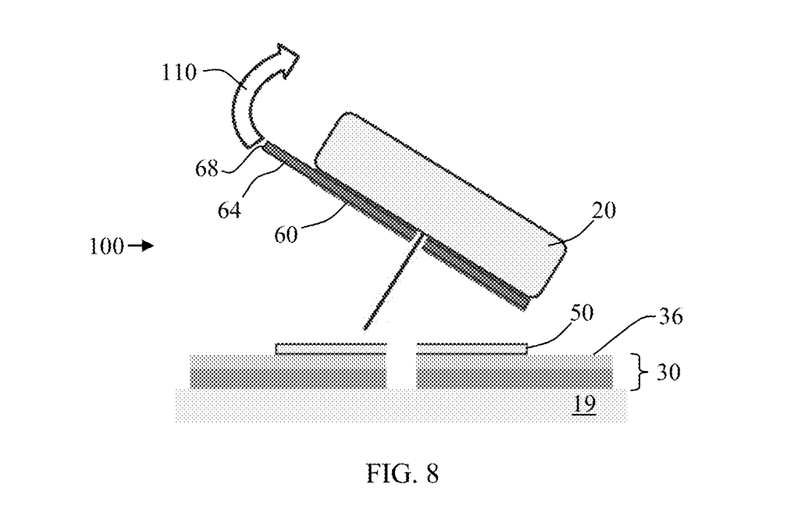
Figure 9:
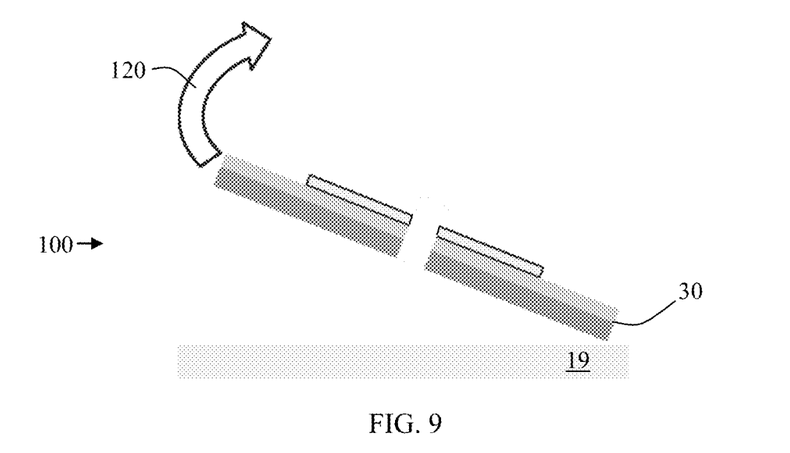
Figure 10:
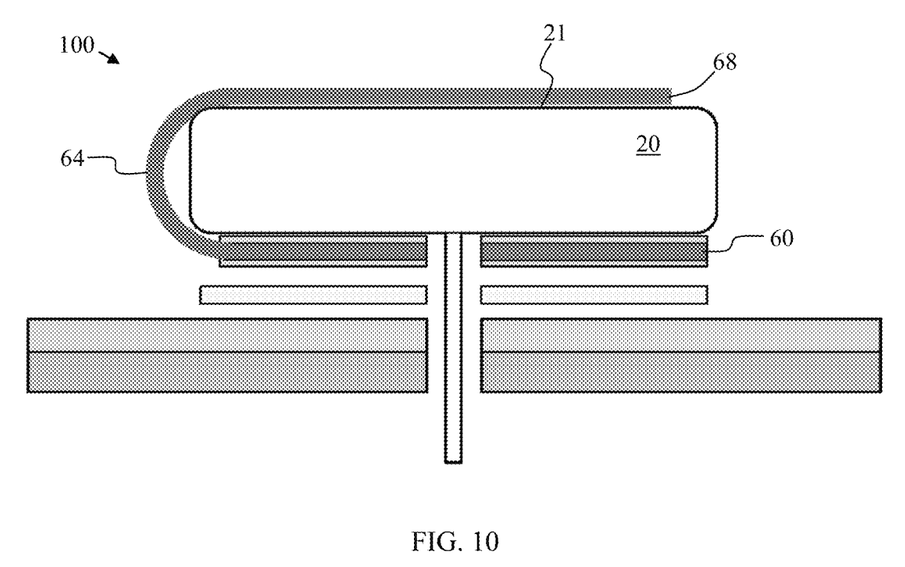
FIG. 10 is an exploded, detailed cross-sectional view of a removable monitoring device in accordance with embodiments herein.

FIGS. 7-9 illustrate a method of using a removable medical device 100. In FIG. 7, the method includes adhering the device 100 to the user's skin 19 to monitor an analyte level. In such an embodiment, the skin adhesive 30 is in direct contact with the skin 19 and the interface component 60 interconnects the durable component 20 and the skin adhesive 30. In an exemplary embodiment, an insertion device may be used to press the top side of the durable component 20 and the top side of the skin adhesive 30 toward the skin 19. Further, a needle or other projection may be advance through the central opening of the durable component 20 and into or alongside the sensor 40 to insert the sensor 40 into the skin 19. The needle may then be withdrawn and the insertion device removed, with the device 100 remaining adhered to the skin 19 and the sensor 40 inserted in the skin 19. The device 100 is then used to monitor an analyte, such as for example glucose.

In FIG. 8, the method continues by separating the device 100 at the interface component 60 and removing the durable component 20 from the skin adhesive 30. For example, a removal force indicated by arrow 110 may be applied to the interface component 60, and specifically to the end 68 of the substrate 64. The adhesive force between the skin adhesive 30 and the skin 19 is greater than the adhesive force between the interface component 60 and the intermediate adhesive 50 (or greater than the adhesive force between the interface component 60 and the backing layer 36 in embodiments in which the intermediate adhesive is above the interface component 60). Therefore, upon application of the removal force to the interface component, the device 100 separates at the interface component 60 while the skin adhesive 30 remains adhered to the skin 19.

Then, the skin adhesive 30 may be treated to reduce the strength of the adhesive force between the skin adhesive 30 and the skin. For example, UV light or other energy may be applied to the skin adhesive to reduce the adhesive force, or a composition, such as a solvent like isopropyl alcohol or other suitable solvent, may be applied to the skin adhesive 30. In either case, the removal of the durable component 20 from the skin adhesive 30 may allow for treatment of an increased area, and possibly the entirety, of the skin adhesive 30 and protects the durable component 20 from damage from such treatment.

FIG. 9 illustrates the removal of the skin adhesive 30 from the skin 19. As shown, a removal force indicated by arrow 120 may be applied to the skin adhesive 30.

It is noted that in certain embodiments of the device 100, the interface component 60 may incorporate a stretch-releasing adhesive. Specifically, the substrate 64 may be a stretchable foam, i.e., the substrate 64 may be an initial length in the longitudinal direction and may be pulled in the longitudinal direction to a greater length. As a result, the strength of the interface adhesive 65 may be reduced. Thus, the method described in FIGS. 7-9 may further include pulling the substrate 64 longitudinally (substantially non-transverse to the user's skin, i.e., generally parallel to the user's skin) to reduce the adhesive force of the interface adhesive 65 before applying the removal force to the substrate 64 to cause the device 100 to separate at the interface component 60 while the skin adhesive remains adhered to the skin.

Figure 11:
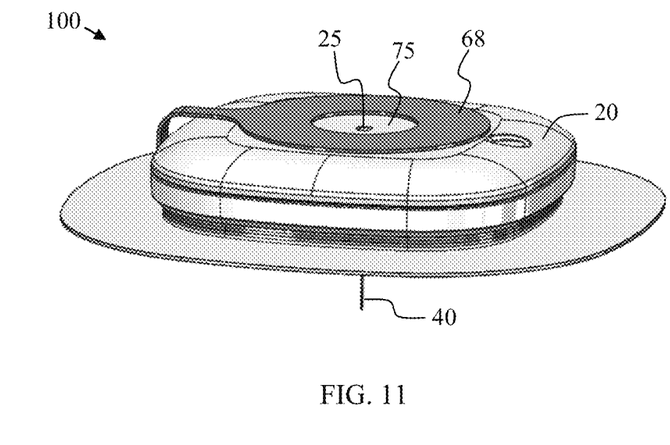
FIGS. 11-13 are perspective views of the removable monitoring device of FIG. 10 illustrating method steps for use thereof.
Figure 12:
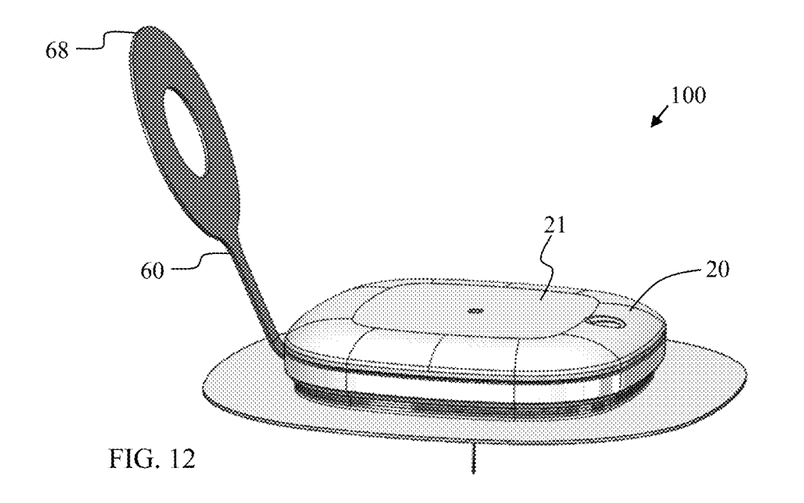
Figure 13:
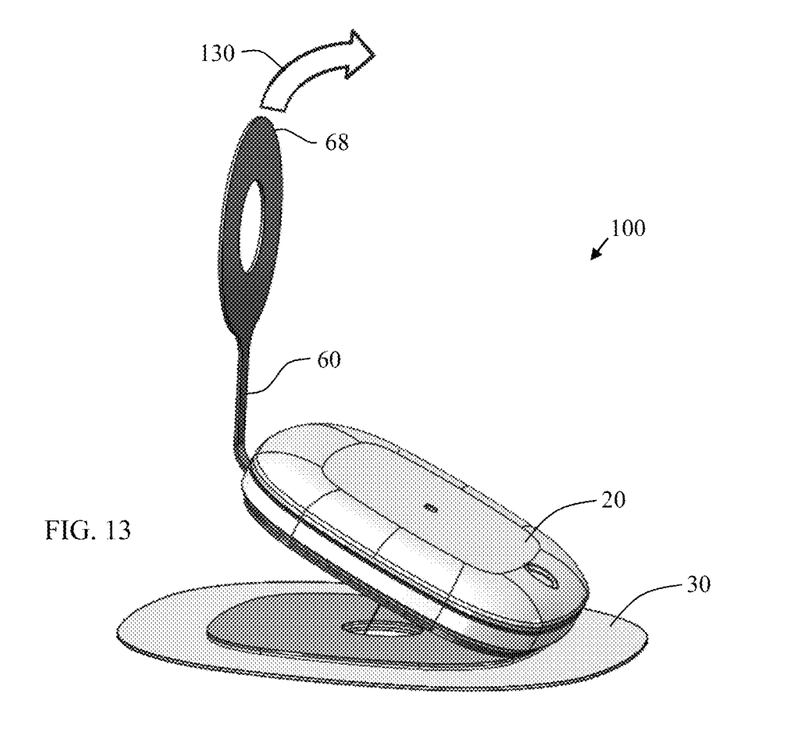

FIGS. 10-13 illustrate another embodiment of the device 100. As shown, the interface component 60 extends for a greater length to the end 68 as compared to the previously illustrated embodiments. As a result, the end 68 may be wrapped back around onto the top side 21 of the durable component 20 and removably attached thereto. In FIG. 11, the end 68 is shown to be formed with a central void 75 aligned with the central opening 25 of the durable component such that a needle may pass through the central void 75 to insert the sensor 40 into the skin. As shown in FIG. 12, when removal of the device 100 from the skin is desired, the end 68 of the interface component is first detached from the top side 21 of the durable component 20. As shown in FIG. 13, the end 68 of the interface component is then pulled with a removal force indicated by arrow 130 to separate and remove the durable component 20 from the skin adhesive 30. The skin adhesive 30 may then be treated and removed as described above.

Figure 14:
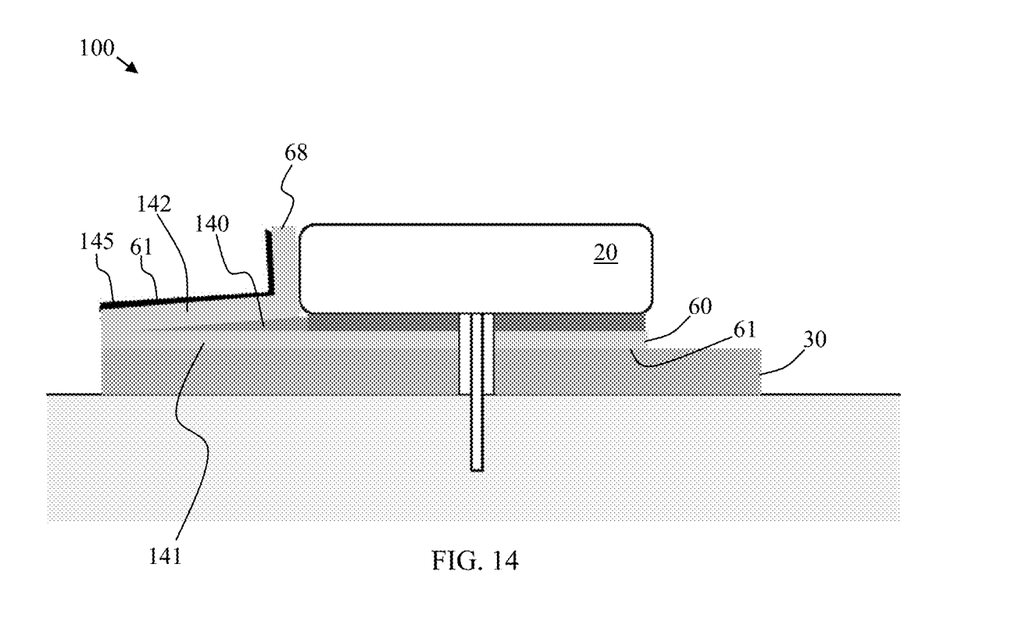
FIG. 14 is a cross-sectional view of a removable monitoring device in accordance with embodiments herein.

FIG. 14 illustrates another embodiment of the device 100. In FIG. 14, the interface component 60 again extends outward from the footprint of the durable component 20 to an end 68. As shown, the interface component 60 may be folded back onto itself. In order to hold the interface component 60 in this configuration, a low tack adhesive 140 may be located between the lower fold (or proximal portion) 141 and the upper fold (or distal portion 142) of the interface component 60. Further, a liner 145 may be located on the upward-facing portion of the bottom side 62 of the interface component 60. When removal of the device 100 is desired, the end 68 of the interface component may be grasped and pulled with a removal force to separate and remove the durable component 20 from the skin adhesive 30 as described above.

Figure 15:
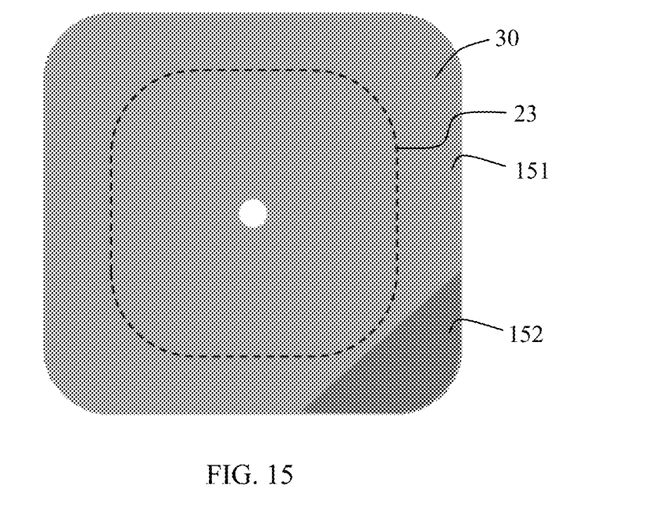
FIG. 15 is a plan bottom view of a removable monitoring device in accordance with embodiments herein.
Figure 16:
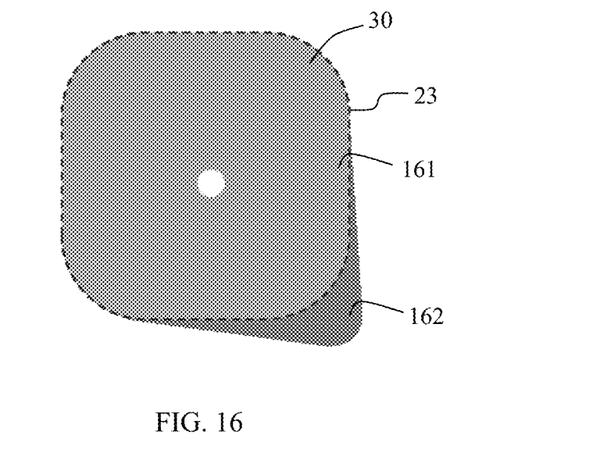
FIG. 16 is a plan bottom view of a removable monitoring device in accordance with embodiments herein.

FIGS. 15 and 16 illustrate embodiments of the skin adhesive 30, specifically in which the skin adhesive 30 is a differential adhesive, i.e., includes more than one area with different adhesive strengths. In FIG. 15, the skin adhesive 30 includes a main region 151 and an edge region 152. In the main region 151, the skin adhesive 30 is provided with a first adhesive strength. In the edge region 152, the skin adhesive 30 is provided with a second adhesive strength that is less than the first adhesive strength. In certain embodiments, the edge region 152 may include no adhesive. As a result, removal of the skin adhesive 30 from the skin is facilitated by first peeling the edge region 152 from the skin and grasping the edge region 152 when removing the main region 151. In the embodiment of FIG. 15, the skin adhesive 30 extends outward from the durable component periphery 23 in all directions, forming an annular portion outside the footprint defined by the durable component periphery 23. In the illustrated embodiment, the edge region 152 is located in the annular portion outside the footprint defined by the durable component periphery 23.

In FIG. 16, the skin adhesive 30 includes a main region 161 located only within the footprint defined by the durable component periphery 23. Further, the skin adhesive 30 includes an edge region 162 outside the footprint defined by the durable component periphery 23. Again, the main region 161 has a first adhesive strength and the edge region 162 has a second adhesive strength that is less than the first adhesive strength. In certain embodiments, the edge region 162 may include no adhesive. As a result, removal of the skin adhesive 30 from the skin is facilitated by first peeling the edge region 162 from the skin and grasping the edge region 162 when removing the main region 161.

For the sake of brevity, conventional techniques related to glucose sensing and/or monitoring and other functional aspects of the subject matter may not be described in detail herein. In addition, certain terminology may also be used in the herein for the purpose of reference only, and thus is not intended to be limiting.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A removable device wearable on a user's skin, the device comprising:
   a skin adhesive configured to adhere to the skin with a first adhesive force;
   a durable component; and
   an interface component interconnecting the durable component and the skin adhesive, the interface component having a first side provided with an interface adhesive and a second side either adhered to an intermediate adhesive or provided with further interface adhesive, wherein the interface adhesive or the intermediate adhesive adheres the interface component to the skin adhesive or to the durable component with a second adhesive force, wherein the first force is greater than the second force such that the device separates at the interface component to remove the durable component from the skin adhesive upon application of a removal force to the device; and
   wherein the durable component includes an insertable member for insertion into the skin, and wherein each of the skin adhesive and the interface component includes a void through which the insertable member extends.

2. The device of claim 1 wherein the interface component comprises a substrate and the interface adhesive is adhered to a side of the substrate, and wherein the intermediate adhesive is located between the durable component and the interface component.

3. The device of claim 1 wherein the interface component comprises a substrate and the interface adhesive adhered to a side of the substrate, and wherein the intermediate adhesive is located between the skin adhesive and the interface component.

4. The device of claim 1 wherein the interface component comprises:
   a substrate, and
   an interface adhesive adhered to each side of the substrate.

5. The device of claim 1 wherein the interface component comprises:
   a substrate,
   wherein the durable component defines a footprint; and
   wherein the substrate extends from within the footprint to outside the footprint to provide a tab for a user to grasp for application of the removal force to the device.

6. The device of claim 1 wherein:
   the durable component has a top side and a bottom side;
   the interface component comprises a substrate;
   the substrate extends from under the bottom side of the durable component to an end that is removably attached to the top side of the durable component; and
   the intermediate adhesive is located between the skin adhesive and the interface component.

7. The device of claim 1 wherein the interface component is perforated with channels.

8. The device of claim 1 wherein the interface component is comprised of a stretchable foam substrate and a stretch-releasing adhesive.

9. The device of claim 1 further comprising a backing layer, wherein:
   the skin adhesive directly contacts the backing layer;
   the intermediate adhesive directly interconnects the backing layer and the interface component;
   the durable component has a top side and a bottom side;
   the interface component comprises a substrate; and
   the substrate extends from a main portion under the bottom side of the durable component to an end that is removably attached to the top side of the durable component.

10. The device of claim 1 wherein the skin adhesive is formed with a main region having a first adhesive force and an edge region having a second adhesive force less than the first adhesive force.

11. The device of claim 1 further comprising a backing layer, wherein the skin adhesive directly contacts the backing layer, and wherein the backing layer is located between the skin adhesive and the interface component.

12. The device of claim 1 wherein the insertable member comprises at least one of a needle or a sensor probe.

13. A removable device wearable on a user's skin, the device comprising:
   a skin adhesive configured to adhere to the skin;
   a durable component having a bottom side; and
   an interface component interconnecting the durable component and the skin adhesive, the interface component having a first side provided with an interface adhesive and a second side either adhered to an intermediate adhesive or provided with further interface adhesive, wherein:
   the interface component extends from under the bottom side of the durable component to an end,
   a distal portion of the interface component is folded onto a proximal portion of the interface component and is removably attached thereto,
   the device separates at the interface component to remove the durable component from the skin adhesive upon application of a removal force to the device, the durable component includes an insertable member for insertion into the skin, and
   each of the skin adhesive and the interface component includes a void through which the insertable member extends.

14. A removable device wearable on a user's skin, the device comprising:
   a skin adhesive configured to adhere to the skin;
   a durable component;
   an interface component interconnecting the durable component and the skin adhesive, wherein the device separates at the interface component to remove the durable component from the skin adhesive upon application of a removal force to the device;
   an intermediate adhesive; and
   a backing layer, wherein:
   the skin adhesive directly contacts the backing layer;
   the intermediate adhesive directly interconnects the backing layer and the interface component;
   the durable component has a top side and a bottom side;
   the interface component comprises a substrate and an interface adhesive adhered to a side of the substrate;
   the substrate extends from a main portion under the bottom side of the durable component to an end that is removably attached to the top side of the durable component; and
   wherein the skin adhesive, the backing layer, the intermediate adhesive, the main portion of the substrate, the end of the substrate, and the interface adhesive are each formed with a central void.

15. A removable device wearable on a user's skin, the device comprising:
   a skin adhesive configured to adhere to the skin;
   a durable component; and
   an interface component interconnecting the durable component and the skin adhesive, the interface component having a first side provided with an interface adhesive and a second side either adhered to an intermediate adhesive or provided with further interface adhesive,
   wherein the device separates at the interface component to remove the durable component from the skin adhesive upon application of a removal force to the device;
   wherein the durable component includes an insertable member for insertion into the skin when the durable component is interconnected with the skin adhesive and the skin adhesive is adhered to the skin;
   wherein the insertable member is removed from the skin when the durable component is removed from the skin adhesive;
   wherein the skin adhesive has a periphery, a first region with a first adhesive strength, and a second region with a second adhesive strength less than the first adhesive strength;
   wherein the periphery of the skin adhesive defines a skin adhesive area; and
   wherein the durable component has a periphery defining a durable component area and underlying footprint, and wherein the second region of the skin adhesive is completely outside of the footprint of the durable component.

16. The device of claim 15, wherein the second region is directly adjacent to the periphery, and wherein the first region of the skin adhesive area is completely within the footprint of the durable component.

17. The device of claim 15 wherein the interface component includes a void through which the insertable member extends.

18. A method for using a removable medical device, the method comprising:
   adhering the device to a user's skin, the device comprising:
   a skin adhesive in direct contact with the user's skin;
   a durable component having an insertable member for insertion into the skin; and
   an interface component interconnecting the durable component and the skin adhesive, the interface component having a first side provided with an interface adhesive and a second side either adhered to an intermediate adhesive or provided with further interface adhesive;
   separating the device at the interface component and removing the durable component from the skin adhesive;
   treating the skin adhesive; and
   removing the skin adhesive from the user's skin.

19. The method of claim 18 wherein treating the skin adhesive comprises applying a solvent to the skin adhesive.

20. The method of claim 18 wherein treating the skin adhesive comprises applying UV light to the skin adhesive.

21. The method of claim 18 wherein:
   the interface component comprises a substrate having a void through which the insertable member extends;
   the durable component defines a footprint;
   the substrate extends from within the footprint to outside the footprint to provide a tab;
   separating the device at the interface component and removing the durable component from the skin adhesive comprises grasping and pulling the tab.

22. The method of claim 18 wherein:
   the durable component has a top side and a bottom side;
   the interface component comprises a substrate;
   the substrate extends from under the bottom side of the durable component to an end that is removably attached to the top side of the durable component; and
   separating the device at the interface component and removing the durable component from the skin adhesive comprises removing the end from the top side of the durable component and grasping and pulling the substrate.

23. The method of claim 18 wherein:
the durable component has a top side and a bottom side;
the interface component comprises a substrate;
the substrate extends from a main portion under the bottom side of the durable component to an end that is removably attached to the top side of the durable component; and
the skin adhesive, the main portion of the substrate, and the end of the substrate are each formed with a central void; and
the method further comprises passing the insertable member through the central void of the end of the substrate to insert a sensor through the central void of the skin adhesive and the interface component and into the user's skin.

24. The method of claim 18 wherein the interface component comprises a stretch-releasing adhesive, and wherein separating the device at the interface component and removing the durable component from the skin adhesive comprises stretching the stretch-releasing adhesive in a longitudinal direction substantially non-transverse to the user's skin.

25. The method of claim 18 wherein the skin adhesive is formed with a main region having a first adhesive force and an edge region having a second adhesive force less than the first adhesive force, and wherein removing the skin adhesive from the user's skin comprises first peeling at least a portion of the edge region from the user's skin before peeling the main region from the user's skin.

26. A method for using a removable medical device, the method comprising:
adhering the device to a user's skin, the device comprising:
a skin adhesive in direct contact with the user's skin;
a durable component; and
an interface component interconnecting the durable component and the skin adhesive;
separating the device at the interface component and removing the durable component from the skin adhesive;
treating the skin adhesive; and
removing the skin adhesive from the user's skin;
wherein:
the durable component has a top side and a bottom side;
the interface component comprises a substrate;
the substrate extends from under the bottom side of the durable component to an end that is removably attached to the top side of the durable component;
the skin adhesive and the interface component are each formed with a central void; and
the method further comprises inserting a sensor through the central void of the skin adhesive and the interface component and into the user's skin.

\* \* \* \* \*